(12) United States Patent
Yokoi et al.

(10) Patent No.: US 8,409,872 B2
(45) Date of Patent: Apr. 2, 2013

(54) CARTRIDGE FOR AUTOMATIC MEASUREMENT AND MEASURING METHOD USING IT

(75) Inventors: Hiroyuki Yokoi, Inashiki-Gun (JP); Takashi Kurihara, Inashiki-Gun (JP)

(73) Assignee: Mitsubishi Chemical Medience Corporation, Tokyo (JP)

( * ) Notice: Subject to any disclaimer, the term of this patent is extended or adjusted under 35 U.S.C. 154(b) by 1905 days.

(21) Appl. No.: 10/281,252

(22) Filed: Oct. 28, 2002

(65) Prior Publication Data

US 2003/0113235 A1  Jun. 19, 2003

Related U.S. Application Data

(63) Continuation of application No. PCT/JP01/03730, filed on Apr. 27, 2001.

(30) Foreign Application Priority Data

Apr. 28, 2000  (JP) ................................. 2000-130767

(51) Int. Cl.
  *G01N 1/38*  (2006.01)
  *G01N 35/00*  (2006.01)
(52) U.S. Cl. ............. 436/179; 422/63; 422/67; 436/180
(58) Field of Classification Search .................... 422/65, 422/102, 63, 67; 435/288.4; 436/179, 180
See application file for complete search history.

(56) References Cited

U.S. PATENT DOCUMENTS

| 4,539,292 | A |   | 9/1985 | Reid et al. |
|---|---|---|---|---|
| 4,714,590 | A |   | 12/1987 | Guigan |
| 5,147,609 | A | * | 9/1992 | Grenner .......................... 422/58 |
| 5,158,895 | A |   | 10/1992 | Ashihara et al. |
| 5,167,922 | A |   | 12/1992 | Long |
| 5,290,708 | A |   | 3/1994 | Ashihara et al. |
| 5,356,525 | A | * | 10/1994 | Goodale et al. ............... 204/602 |
| 5,358,691 | A |   | 10/1994 | Clark et al. |
| 5,482,839 | A |   | 1/1996 | Ashihara et al. |

(Continued)

FOREIGN PATENT DOCUMENTS

| CN | 86 1 01694 | 10/1986 |
|---|---|---|
| EP | 0 449 321 | 10/1991 |

(Continued)

OTHER PUBLICATIONS

Derwent Abstracts of Japan, JP 7-505475, Jun. 15, 1995.

(Continued)

*Primary Examiner* — In Suk Bullock
*Assistant Examiner* — Paul Hyun
(74) *Attorney, Agent, or Firm* — Oblon, Spivak, McClelland, Maier & Neustadt, L.L.P.

(57) ABSTRACT

A cartridge for use in measuring a component to be measured contained in a sample includes a diluting well for diluting a predetermined amount of the sample to a desired dilution, and a reaction well in which the component to be measured contained in the sample and a substance specifically reacting therewith are allowed to react. A diluting solution is filled in the diluting well in a predetermined amount to provide the desired dilution based on a type of the component to be measured when the predetermined amount of the sample is dispensed in the diluting well by a uniform operation.

8 Claims, 2 Drawing Sheets

TOP VIEW

SIDE SECTIONAL VIEW

U.S. PATENT DOCUMENTS

| | | | |
|---|---|---|---|
| 5,482,861 A | 1/1996 | Clark et al. | |
| 5,483,075 A * | 1/1996 | Smith et al. | 250/458.1 |
| 5,885,529 A | 3/1999 | Babson et al. | |
| 6,143,250 A | 11/2000 | Tajima | |
| 6,337,053 B1 | 1/2002 | Tajima | |
| 2002/0155616 A1 | 10/2002 | Hiramatsu et al. | |

FOREIGN PATENT DOCUMENTS

| | | |
|---|---|---|
| JP | 3-181853 | 8/1991 |
| JP | 3-292880 | 12/1991 |
| JP | 4-218775 | 8/1992 |
| JP | 8-122336 | 5/1996 |
| JP | 2731613 | 3/1998 |
| JP | 11-174056 | 7/1999 |
| JP | 11-316226 | 11/1999 |
| JP | 3010509 | 2/2000 |
| JP | 3206442 | 9/2001 |
| JP | 2001-318101 | 11/2001 |
| JP | 2001-349896 | 12/2001 |
| WO | WO 92/22802 * | 12/1992 |
| WO | WO 93/20443 | 10/1993 |
| WO | WO 97/05492 | 2/1997 |
| WO | WO 97/47388 | 12/1997 |

OTHER PUBLICATIONS

Japanese Office Action mailed on Aug. 9, 2011, issued for JP Application No. 2008-144877 (with English translation).

Office Action issued Apr. 12, 2011, in Japanese Patent Application No. 2008-144877, with English abstract.

* cited by examiner

CARTRIDGE FOR AUTOMATIC MEASUREMENT AND MEASURING METHOD USING IT

CROSS REFERENCE TO RELATED APPLICATION

This is a Continuation Application of PCT Application No. PCT/JP01/03730, filed on Apr. 27, 2001, which was not published under PCT Article 21(2) in English. This application is based upon and claims the benefit of priority from the prior Japanese Patent Application No. 2000-130767, filed Apr. 28, 2000, the entire contents of which are incorporated herein by reference.

TECHNICAL FIELD

The present invention relates to a cartridge for automatic measurement which is used by putting it in an automatic measuring device for automatically determining a component contained in a sample, and to an automatic measuring method using the cartridge for automatic measurement.

BACKGROUND ART

Heretofore, various analyzers for automatic analysis of human blood have been developed. Such analyzers greatly differ in analyzable concentration ranges for different items to be analyzed (for example, from mg/ml to pg/ml). Depending on respective items to be analyzed, different analyzing methods (measuring principles) have been selected from, for example, an enzyme immunoassay (EIA) method, a latex immunoassay (LIA) method, a turbidimetric immunoassay (TIA) method, and a fluorescence immunoassay (FIA) method, a chemiluminescent enzyme immunoassay (CLEIA) method in consideration of the concentration of the objective substances. Furthermore, there are items to be analyzed, for which a sample in the form of an undiluted solution is measured as it is, and there are also items to be analyzed, for which dilution of a sample is needed prior to measurement of the sample. Recently, instruments which can cover a plurality of kinds of items to be analyzed and a wide range of concentration by themselves alone have come to be developed.

However, in the aforementioned instruments which perform multi-item processing by themselves alone, although a sample-dispensing device, a reagent-dispensing device, a reaction well, etc. are shared, several kinds of modules corresponding to the measuring principles are integrated in a single instrument, thus making the instrument to have a very complicated mechanism and be a large-scaled one. The complicated mechanism leads particularly to an increase in the number of operating parts, which naturally results in an increase in trouble such as breakdown. Thus, daily maintenance and inspection as well as management of the precision of the instrument become a big load. In addition, different measuring principles will naturally require different analysis processes for controlling the amount of a sample, the kind of a reagent, the amount of a reagent, the condition of stirring, the condition of separating a reaction product and an excess reagent from each other (B/F separation), the reaction time, the measuring method, etc. depending on the respective items to be analyzed. It is essentially impossible for a single instrument to perform a plurality of different analyzing processes concurrently; under the present circumstances, progress of individual analyzing processes is strictly controlled so that different analyzing processes should not interfere with each other. Therefore, in the case where samples whose items to be analyzed differ from each other are to be concurrently measured, waiting time (waiting state) is required, which leads to a decrease in throughput capacity, which is a cause of a considerable increase in time required for measurement.

In addition, two to six kinds of reagents are to be used for each item for analyzing, in general. This imposes a great load to the operator in preparation before measurement.

In summary, in the conventional instruments, the complexity of their mechanism increases the load of their maintenance and production cost thereof, as well as the time required for measurement and the time and manpower for preparing necessary reagents. These become big problems particularly, for example, in emergency testing and in point of care testing (POCT) that physicians/nurses perform.

To cope with such problems, a "one test-one cartridge" type cartridge for automatic measurement having filled with all the reagents necessary for measurement in the form of solutions, respectively, has been proposed (JP 11-316226 A). However, no method for coping with different dilutions, which will be required depending on items to be analyzed, has been proposed yet.

DISCLOSURE OF THE INVENTION

Under the aforementioned circumstances, an object of the present invention is to provide a cartridge for automatic measurement used for an automatic measuring instrument capable of being used for measuring a plurality of kinds of items to be analyzed requiring different dilutions in a sample without substantially increasing a measuring time even when these items are measured concurrently in an instrument having only mechanisms simplified as much as possible, and a measuring method using this cartridge.

The inventors of the present invention have found that by providing a cartridge with a diluting well for diluting a sample, and diluting a predetermined amount of the sample to a desired dilution in the diluting well, the mechanisms of the automatic measuring instrument can be simplified, and the time required for measurement is prevented from substantially increasing even when a plurality of kinds of items to be analyzed are measured concurrently, thus achieving the present invention.

Therefore, according to the present invention, there is provided a cartridge for use in measuring a component to be measured contained in a sample, comprising at least a diluting well for diluting a predetermined amount of the sample to a desired dilution; and a reaction well in which the component to be measured in the sample and a substance specifically reacting therewith are allowed to react.

Preferably, two or more lines of well groups are arranged in parallel, each well group comprising a diluting well and a reaction well.

Preferably, a cartridge has a reagent-containing well for containing a reagent necessary for the measurement, a sample-dispensing well for dispensing a sample, a washing well for performing washing a reaction product, and/or a measuring well for performing measurement of the reaction product.

Preferably, a cartridge is usable in measurement in combination with another cartridge filled with a reagent and/or a solution which are/is necessary for measurement of the component to be measured contained in the sample.

Preferably, all of the reagent and/or the solution which are/is necessary for measurement of the components to be measured contained in the sample are sealed.

Preferably, the reaction between the component to be measured and the substance specifically reacting therewith is an immunological reaction.

Preferably, the immunological reaction is a reaction in which the component to be measured in the sample and the substance immunologically specifically reacting therewith are allowed to react to form a first immune complex, and the first immune complex and a label immunologically specifically reacting therewith are allowed to react to form a second immunological complex.

According to another aspect of the present invention, there is provided a measuring method for a component to be measured contained in a sample, comprising the steps of dispensing the sample containing the component to be measured in a cartridge of the present invention; diluting the sample to a desired dilution on the cartridge; reacting the component to be measured in the diluted sample and a substance specifically reacting herewith; and measuring an amount of a reaction product.

Preferably, a plurality of kinds of different components to be measured are concurrently measured by using a cartridge having two or more lines of well groups, each well group comprising a diluting well and a reaction well, or by using a plurality of cartridges.

Preferably, the measurement is performed by using the cartridge of the present invention and another cartridge filled with a reagent and/or a solution necessary for the measurement of the component to be measured contained in a sample.

Preferably, the reaction between the component to be measured and the substance specifically reacting therewith is an immunological reaction.

Preferably, the immunological reaction is a reaction in which the component to be measured in the sample and the substance immunologically specifically reacting therewith are allowed to react to form a first immune complex, and the first immune complex and a label immunologically specifically reacting therewith are allowed to react to form a second immunological complex, and wherein the amount of the label in the second immune complex formed by the reaction is measured.

According to still another aspect of the present invention, there is provided a measuring instrument comprising at least a cartridge-accommodating section for accommodating a cartridge of the present invention; a dispensing section for dispensing a reagent and/or a sample to the cartridge accommodated by the cartridge-accommodating section, and a measuring section for measuring a reaction product on the cartridge accommodated by the cartridge-accommodating section.

BEST MODE FOR CARRYING OUT THE INVENTION

Figure 1:
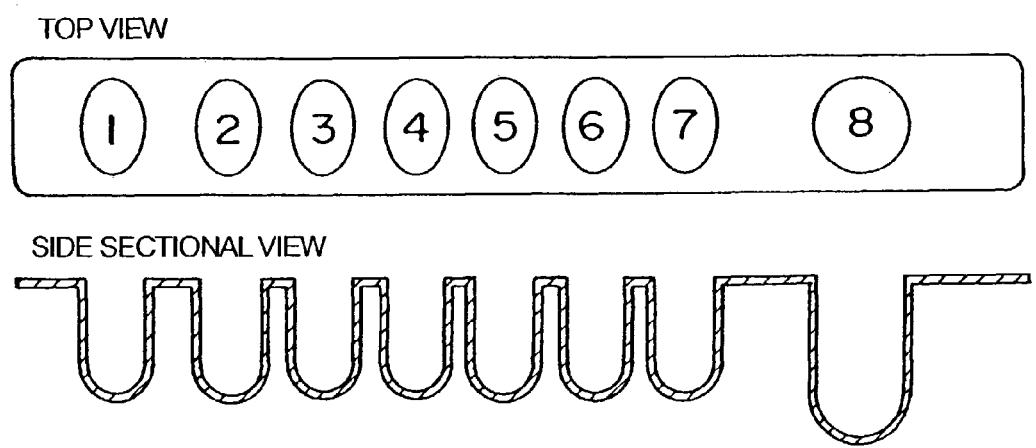
FIG. 1 is a diagram of a cartridge according to Example 1. Symbols in the figure are as follows. 1 denotes a sample-dispensing well; 2, a diluting well 1; 3, a diluting well 2; 4, a magnetic particles-containing well (reaction well 1); 5, a washing well 1; 6, a labeled antibody-containing well (reaction well 2); 7, a washing well 2; and 8, a photometric well.

The terms used herein have the following meanings unless otherwise indicated specifically.

The cartridge of the present invention is used when a component to be measured contained in a sample is measured, and usually it is used so as to be set in an automatic measuring instrument.

The aforementioned measurement is performed usually by the method for measuring a component to be measured according to the present invention, which method comprises the steps of dispensing a sample containing a component to be measured, diluting the sample, reacting the component to be measured contained in the sample with a substance which specifically reacts therewith, and measuring the amount of a reaction product.

The component to be measured is not particularly limited and any component may be used so far as there exists a substance specifically reacting with the component. Examples of combination of a component to be measured and a substance which specifically reacts therewith include an antigen and an antibody, an antibody and an antigen, an enzyme and a substrate, a sugar chain and a lectin, etc. Thus, in the present invention, the expression "specifically reacts or specifically reacting" means biochemical specific binding. The component to be measured or the substance specifically reacting therewith may be a substance whose chemical nature will change between before and after the binding, such as substrates.

The sample may be any sample so long as it contains a component to be measured or has a possibility of containing it. Examples thereof may include blood, serum, plasma and urine.

Conditions of, for example, the step of reacting the component to be measured and the substance which specifically reacts therewith, and the step of measuring the amount of the reaction product, etc. may be selected appropriately depending on the combination of the component to be measured and the substance which specifically reacts therewith. For example, the reaction between an enzyme and a substrate and measurement of the amount of a reaction product can be performed by mixing the enzyme with the substrate to allow the enzyme to act on the substrate and measuring the amount of the reaction product (decomposition product of the substrate). The reaction between an antibody and an antigen and measurement of the amount of a reaction product can be performed by mixing the antibody or antigen with a solid phase carrier having bound thereto a corresponding antigen or antibody and a label to form a reaction product (immune complex), washing the reaction product to remove unused antibody or antigen and unused label from the immune complex (B/F separation), and measuring the amount of the label bound to the solid phase by the formation of the immune complex. Thus, in the present invention, the expression "measuring the amount of a reaction product" encompasses not only directly measuring the amount of a reaction product itself but also measuring the amount of a substance quantitatively related to the amount of the reaction product. From the thus-measured amount of the reaction product, the amount of the component to be measured in the sample can be calculated.

The cartridge of the present invention is characterized in that it comprises at least a diluting well for diluting a predetermined amount of a sample to a desired dilution and a reaction well for reacting a component to be measured in the sample with a substance specifically reacting with the component.

As mentioned above, the dilution of a sample may differ depending on the component to be measured (item to be analyzed). However, when the cartridge of the present invention is used, it is only needed to dispense a predetermined amount of a sample in measuring operation regardless of which ever the item to be analyzed may be, since the cartridge is provided with a dilution well for diluting a predetermined amount of the sample to a desired dilution. This reduces the efforts by the operator required for confirming the dispensing amount. Also, this considerably reduces the possibility of failure of measurement due to an error in the dispensing amount. In an automatic measuring instrument which uses the cartridge of the present invention by incorporating it therein, the mechanism of changing the dispensing amount of a sample depending on the item to be analyzed becomes no longer necessary, so that the mechanisms can be simplified. In the present invention, it is apparent that where no diluting solution is filled in the diluting well, the stock solution is left as it is (that is, dilution is 1). Therefore, the expression "dilution" herein is used in a sense so as to encompass leaving the stock solution as it is. In the case where dilution of sample at a high dilution is performed, it is preferred that two or more dilution wells be provided in the cartridge and two-stages or more dilutions be performed.

As stated above, the cartridge of the present invention includes one which is capable of handling different conditions for analyzing by a uniform operation and furthermore one which is provided with two or more lines of well groups required for the measurement of components to be measured arranged in parallel. Alternatively, measurement of a plurality of kinds of different components to be measured can be performed concurrently by using a plurality of cartridges. Therefore, when the cartridge of the present invention is used, neither the time required for the measurement will increase considerably even in the case of measurement of a plurality of kinds of different components to be measured nor the mechanisms of the automatic measuring instrument to be used will be changed.

The dilution of a sample and a diluting solution to be filled in the diluting well may be appropriately selected depending on, for example, the kinds of the sample, components to be measured, and substances specifically reacting with the components to be measured. The diluting solution may contain a reagent necessary for pretreatment of the sample. If it does, dilution and pretreatment are concurrently performed in the diluting well.

The cartridge of the present invention may have a reagent-containing well for containing a reagent necessary for the measurement of the component to be measured contained in the sample. The reagent-containing well may also serve as a reaction well. In other words, a portion of the reagent which participates in the reaction may be contained in a reaction well. The reagent to be contained in the reagent-containing well or the reaction well may include one species or a plurality of species so far as the contained reagents do not react with each other. The reagent to be contained may be liquid (for example, solution or suspension), or solid so far as it can be dissolved or suspended in the solution to be injected in the well.

It is preferred that the cartridge of the present invention has further a sample-dispensing well for dispensing a sample. With this construction, a predetermined amount of the sample can be added by a uniform process to the diluting well from the sample-dispensing well to which the sample has been dispensed. In addition, when a sample is dispensed to the cartridge from a container in which the sample has been collected, strict control of the amount of the sample becomes unnecessary and the operation by the operator becomes easy. Furthermore, in the automatic measuring instrument in which the cartridge of the present invention is set, it is unnecessary to provide an additional mechanism such as a mechanism of directly quantitating and dispensing the sample from a master sample container outside the cartridge in order to dispense a predetermined amount of the sample, so that the mechanisms can be simplified.

The cartridge of the present invention may also have a measuring well for measuring the amount of a reaction product. For example, a photometric well for optical measurement may be provided. Here, in the case where a special measurement condition is desired, for example, the case where the measurement must be performed under dark conditions, the measuring well may be provided in a separate cartridge or in a separable form.

The shape and size of the cartridge of the present invention are not particularly limited. However, for easy handling by the operator, the cartridge is preferably of, for example, a boat form in which a reagent-containing well, a sample-dispensing well, a diluting well, a reaction well and/or a measuring well are/is linearly arranged. A plurality of wells may be used for each type of well. Furthermore, for the measurement of a plurality of kinds of items to be analyzed, the cartridge of the present invention which has two or more lines of necessary well groups arranged in parallel as described above may be used. The material of the cartridge of the present invention is not particularly limited but a transparent material is preferred since optical measurement is possible through the wall of the cartridge.

In the cartridge of the present invention, the reaction between the component to be measured and the substance specifically reacting therewith are preferably an immunological reaction. That is, it is preferred that the component to be measured and the substance specifically reacting therewith are an antibody and an antigen.

The immunological reaction is preferably one in which a component to be measured in a sample is reacted with a substance specifically reacting therewith to form a first immune complex and then the first immune complex is reacted with a label immunologically specifically reacting therewith to form a second immune complex. In this case, the cartridge of the present invention preferably has a reaction well for forming the first immune complex and a reaction well for forming the second immune complex. More preferably, the cartridge of the present invention has washing wells for B/F separation corresponding to the respective reaction wells. The washing wells may be filled with a washing solution in advance or filled by dispensing from, for example, another cartridge or bottle.

The reagent and/or the solution necessary for the measurement of the component to be measured contained in a sample used in the present invention may be filled in another cartridge in advance and the cartridge may be used in combination with the cartridge of the present invention in performing measurement. Measurement can be performed, for example, by filling a diluting solution of a sample, a substance and a label specifically reacting with the component to be measured in the sample, and a washing solution, etc. for washing the resultant immune complex in another cartridge in advance, and dispensing the reagent and/or the solution to the cartridge of the present invention by a uniform operation. By such a method, the mechanism of the instrument can be simplified and the structure of the cartridge of the present invention can be simplified and downsized. In addition, it becomes easy to solve the problem on the storage stability of the reagent and/or the solution to be used. Of course, it is possible to fill the reagents and/or solutions necessary for measurement into both of the cartridge of the present invention and the other cartridge and use them in combination.

All of the reagents and/or the solutions necessary for the measurement of the component to be measured contained in the sample may be filled in the cartridge of the present invention. It is preferred that all the necessary reagents, for example, a diluting solution of a sample, a substance and a label specifically reacting with the component to be measured in the sample, and a washing solution, etc. for washing the resultant immune complex be filled in the cartridge of the present invention in advance. By so doing, use of one cartridge for one component to be measured enables handling all the cases, so that wastes of reagents can be cut. Supply of water or discharge of water become unnecessary, leading to further simplification of the measuring instrument and to reduction in time required for the measurement.

It is preferred that the cartridge of the present invention, when it is filled with, for example, reagents and/or solutions, and the like such as a diluting solution, a label, a washing solution, and the like in advance, is preferably sealed with an aluminum laminate foil, a plastic film or the like on its top in order to prevent contamination of foreign matter and evaporation/deterioration of reagents. Seals of aluminum laminate foil are particularly preferred since they can be easily opened automatically by a perforating mechanism in the automatic measuring instrument. In the case where the reagent(s) and/or solution(s) and the like are filed in another cartridge and measurement is performed using the cartridge in combination, it is preferred that the cartridge also be sealed.

On the cartridge of the present invention, a bar code encoding information on the sample, information on the items to be analyzed, information on the management of the reagent, etc. may be attached by printing, applying or the like. Attaching such a bar code on the cartridge makes the following possible: when using an automatic measuring instrument which recognizes the bar code on the cartridge and automatically select an item for analyzing, the operator can measure an any item or items to be analyzed easily and efficiently by using a single automatic measuring instrument by merely selecting an appropriate cartridge or cartridges. This also eliminates the need for performing work sheet operation which has been a major cause for erroneous setting of items to be analyzed as has been performed in the conventional common automatic measuring instruments and enables performing the measurement of a plurality of kinds of items to be analyzed without fail and with ease. Furthermore, storage and management of reagents become easy.

In the measuring method of the present invention, in the case where the sample contains a plurality of kinds of components to be measured, it is preferred to concurrently measure the plurality of kinds of different components to be measured by using a plurality of cartridges or a cartridge in which two or more lines of well groups are arranged in parallel. In such a case, it is preferred that use be made of an automatic measuring instrument which is capable of concurrently measuring a plurality of items to be analyzed in parallel and in which a plurality of the cartridges of the present invention can be set, or an automatic measuring instrument or in which the cartridge of the present invention having wells corresponding to a plurality of items to be analyzed (two or more lines of well groups being arranged in parallel) can be set in.

In the automatic instrument in which the cartridge or cartridges of the present invention are set when in use, known means may be used, respectively, for means for aspirating a predetermined amount of a liquid from one well and dispensing it to another well, means for mixing the content in the well, means for performing B/F separation, means for measuring the amount of a reaction product or of a label, means for calculating the amount of the component to be measured from the result of the measurement of the amount of the reaction product or of the label, means for controlling the temperature of a cartridge, means for recognizing a bar code, means for concurrently performing measurement of a plurality of cartridges, and so on.

Hereinafter, the present invention will be illustrated referring to an example of immunoassay, more particularly, chemiluminescent enzyme immunoassay (CLEIA), according to one example of a preferred aspect.

A cartridge according to a preferred aspect is a cartridge for automatic measurement to be used so as to be set in an automatic measuring instrument that automatically quantitates a component to be measured in a sample. This cartridge has a reaction well for reacting the component to be measured with the substance immunologically specifically reacting therewith, a plurality of reagent-containing well for filling reagents, respectively, to be used in the reaction, a sample-dispensing well for dispensing a sample, a diluting well for diluting the sample, a washing well for performing B/F separation, and/or a photometric well. As described above, the reagent-containing well may also serve as a reaction well. Preferably these wells are used as follows. The diluting well is filled with a diluting solution in an amount sufficient for diluting a predetermined amount of the sample to a desired dilution. A plurality of reagent-containing wells are individually filled with a solid phase carrier for carrying out immunologically specific reaction, a labeled antigen or antibody, a reagent for performing the measurement of the amount of the label, etc. The washing well is filled with a washing solution for washing immune complexes.

In the reagent-containing well of the cartridge, for example, a solid carrier (sensitized solid phase) having bound thereto an antigen or antibody is placed, so that the well can also serve as a reaction well. The solid phase carrier may include polystyrene beads, magnetic particles and the like which have been conventionally used in immunoassays. Furthermore, it is also possible that no solid phase carrier is added to the well but an antibody or antigen is used so as to be immobilized to the inner wall of the well.

The immunoassay to be used in the present aspect is preferably a chemiluminescent enzyme immunoassay (CLEIA) which is advantageous in respect of sensitivity. The solid phase carrier preferably comprises magnetic particles the B/F separation of which can be easily performed by means of a magnet. The B/F separation can be performed by application of a magnetic field to the cartridge from outside thereof by use of a permanent magnet, an electromagnet or the like. Also, as disclosed in JP 11-262678 A, application of a magnetic field can be performed by utilizing a magnet provided on the aspiration and dispense sides of the pipette tip, etc., of the dispenser.

The other reagent-containing wells may also serve as a reaction well by adding thereto a labeled antigen or antibody. For example, examples of the label include enzymes radioisotopes, coloring substances, fluorescent substances, and luminescent substances, various colored particles. In chemiluminescent enzyme immunoassays (CLEIA), enzymes are preferably used. Examples of such a labeling enzyme include alkaline phosphatase, peroxidase, galactosidase, and glucooxidase. As substrates for the labeling enzymes, those substrates which correspond to respective enzymes are suitably used. For example, adamantyl methoxyphenyl phosphoryl dioxetane (AMPPD) can be used for alkaline phosphatase, luminol/peroxide can be used for peroxidase, and adamantyl methoxyphenyl-β-D-galactosyldioxetane (AMPGD) can be used for galactosidase.

When using a diluting well, it is preferred that a predetermined amount of diluting solution for each item for analyzing be filled in advance in the diluting well. For example, in the case where two different items to be analyzed, i.e., hepatitis C virus (HCV) antibody and HBs antigen (HBsAg) are to be measured, identically setting the amount of a sample, the amount of reagent solution of the solid phase carrier, the amount of reagent solution of labeled antigen or antibody, the amount of washing solution, and measuring conditions for labels, etc. for both of the two items and using a cartridge with the amounts of the diluting solution filled in diluting wells being different for the two items in an automatic measuring instrument provided with two or more mechanisms for performing a series of immune reaction processes in parallel enables concurrent processing of both of the two items by the same analyzing step.

In the case where a high dilution of a sample is to be performed, it is preferred that two or more diluting wells be provided on the cartridge so as to perform two or more stages dilution be performed. FIG. 1 illustrates an example of such a cartridge. That is, in the case of HCV antibody, since a relatively large amounts of components to be measured exist in a sample hence it is necessary to measure the sample after preliminarily diluting it, a cartridge for an HCV antibody with a diluting well 1 (2) in which 500 μl of a diluting solution is filled in advance and a diluting well 2 (3) in which 335 μl of the diluting solution is filed in advance is used. The sample in an amount of 70 μl is aspirated from a sample-dispensing well (1) and the whole 70 μl of it is dispensed to a diluting well 1 (2) by means of liquid aspirating/dispensing mechanisms of the automatic measuring instrument and is mixed with 500 μl of the diluting solution, giving an about 8.1 fold dilution (570/70=8.14) in this first stage dilution. Then, 65 μl of the sample diluted in the first stage is aspirated from the diluting well 1 (2) and the whole amount of it is dispensed in the diluting well 2 (3) and mixed with 335 μl of the diluting solution. In this second stage dilution, the sample is finally diluted about 50 folds (570/70×400/65=50.1). Lastly, 60 μl of the sample diluted in the second stage is aspirated from diluting well 2 (3), and 60 μl of the sample finally diluted 50 times is dispensed in a reaction well (4). On the other hand, HBsAg is an item for analyzing that requires high sensitivity, the sample is used as it is in a form of stock solution without dilution. By using a cartridge for HBsAg in which nothing is filled in both of the diluting well 1 (2) and the diluting well 2 (3), 70 μl each of the sample is aspirated in the same manner as the aforementioned HCV antibody and simultaneously therewith from the sample-dispensing well (1) and the whole 70 μl of it is dispensed to the diluting well (2) and then 65 μl is aspirated from the diluting well 1 (2) and the whole amount of it is dispensed to the diluting well 2 (3). Lastly, 60 μl is aspirated from the diluting well 2 (3) and the whole 60 μl is dispensed to the reaction well. Since the diluting well is not filled with a diluting solution, the dilution of the sample is not performed and finally a 60 μl portion of the sample as a stock solution is dispensed to the reaction well (4). Thus, in the present invention, it is possible to concurrently measure different items to be analyzed even by using an instrument which performs only a single style of analyzing process.

Of course, the dilution of a sample is not limited to 50 folds as in the aforementioned example but may be changed to a desired dilution of 1 or more folds depending on the amount of the diluting solution to be filled in the dilution well. In order that a predetermined amount is introduced exactly into the reaction well even where the dilution is 1 in consideration of adhesion to the wall of a well, it is preferred that the amount of aspiration is set smaller than the amount of dispense in the diluting well.

Figure 2:
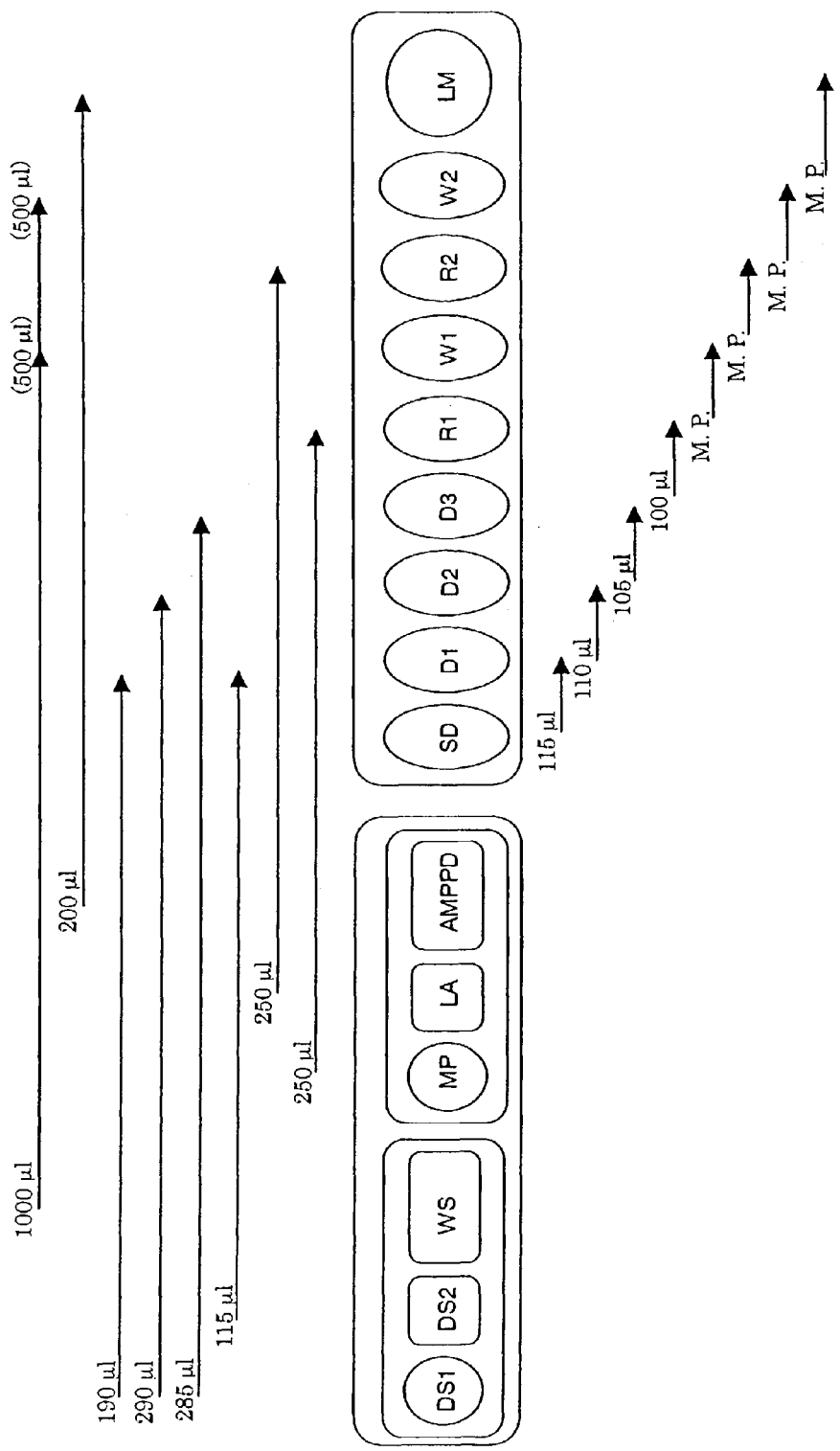
FIG. 2 is a diagram of a cartridge according to Example 2 and illustration of operating conditions therefor. Operation of filling of reagents is described above the cartridge, and operation of dilution of a sample and reaction is described below the cartridge. Symbols in the figure are as follows. DS1 denotes a diluting solution-containing well 1; DS2, a diluting solution-containing well 2; WS, a washing solution-containing well; MP, a magnetic particles-containing well; LA, a labeled antibody-containing well; AMPPD, an AMPPD-containing well; SD, a sample-dispensing well; D1, a diluting well 1; D2, a diluting well 2; D3, a diluting well 3; R1, a reaction well 1; W1, a washing well 1; R2, a reaction well 2; W2, a washing well 2; LM, a photometric well; and M.P., magnetic particles.

As aforementioned, measurement may be performed by using in combination of the cartridge of the present invention and another cartridge in which a reagent and/or a solution necessary for the measurement are/is filled. For example, the cartridge of the present invention having a sample-dispensing well, a dilution well, a reaction well, a washing well and a photometric well is used without filling any reagent and/or solution therein. On the contrary, a diluting solution, a solid phase carrier, a labeled antigen or antibody, a reagent for measuring the amount of a label, etc. are filled in another cartridge, from which they are dispensed by performing dispensing operation and measurement can be performed in the same manner as above. FIG. 2 shows an example of a cartridge of this aspect.

In the sample diluting step, pretreatment of a sample may be performed by adding an acid, an alkali, an organic solvent, a protein denaturant, a detergent, etc. to the diluting solution. For example, in the case where blood (whole blood) is used as a sample, it is preferred that the pretreatment be performed by adding any desired detergent, etc. since blood contains a large amount of interference and for some other reasons. By concurrently performing the dilution and pretreatment of the sample in this manner, high precision measurement can be easily performed even when blood and the like are used as samples. As a result, the present invention can be preferably used in emergency tests and point of care testing (POCT) to be performed by physicians and nurses.

The washing solution for the washing off of unreacted sample and label from immune complexes (B/F separation) requires much expense in time and effort for preparing the washing solution, supplementing it during measurement and disposal of waste liquid when the washing solution is supplied from a part of devices in the automatic measuring instrument as seen in the conventional automatic measuring instrument. The washing solution used in the conventional automatic measuring instrument standardized with respect to the composition and liquid amount of the washing solution regardless of items to be analyzed, so that it is impossible to adopt optimal composition of the washing solution for each item for analyzing. From the aforementioned points, it is preferred that the washing solution also be contained in a cartridge. However, in the case where, for example, the composition or the liquid amount is identical, the washing solution may be uniformly supplied from a part of devices in the automatic measuring instrument as described above.

For accelerating the reaction, it is preferred that a mechanism for maintaining the cartridge of the present invention at a necessary temperature, for example, in a range of 35 to 45° C. which is suitable for enzymatic reactions be attached to the automatic measuring instrument in which the cartridge of the present invention is set when in use.

The measurement of labels may be performed as follows. For example, in the case of chemiluminescent enzyme immunoassay, the measurement can be performed directly through a photometric well by use of a photomultiplier, etc., after mixing an immune complex and a substrate for a labeling enzyme. In the case of enzyme immunoassay, the measurement can be performed after mixing an immune complex with an enzyme substrate solution by irradiating measuring light having a wavelength to be measured from a bottom or side of the measuring well and measuring transmitted light that passed through the photometric well.

The automatic measuring instrument in which the cartridge of the present invention is set when in use includes at least a cartridge-accommodating section for accommodating a cartridge, a dispensing section for dispensing a reagent and/or a sample to the cartridge accommodated in the cartridge-accommodating section, and a measuring section for measuring a reaction product on the cartridge accommodated in the cartridge-accommodating section. The cartridge-accommodating section may be the same as a conventional cartridge-accommodating section except that it is made to have a structure capable of accommodating the cartridge of the present invention. The dispensing section is constituted by conventional mechanisms such as liquid aspirating/dispensing mechanisms, etc. corresponding to the kinds and properties of a reagent and/or a sample. The term "dispensing" as used herein encompasses both of the following: transferring a reagent and/or a sample from outside a cartridge to a well on the cartridge, and transferring a reagent and/or a sample from one well to another well on a cartridge. The measuring section is constituted by conventional mechanisms such as photometric mechanisms depending on the kinds and properties of a reaction product. In the case where the measurement is performed by using the cartridge of the present invention having provided thereon two or more lines of well groups in parallel or a plurality of the cartridges of the present invention, the automatic measuring instrument is preferably an instrument having provided in parallel therein a plurality of mechanisms for performing a series of immune reactions and capable of concurrently operating and controlling the processes of, for example, dispensing a sample, diluting the sample, dispensing a reagent, B/F separation and photometry. In this manner, even in the case of immunoassays, a plurality of items to be analyzed can be concurrently measured by using an instrument which performs only a single style of analyzing process without substantially increasing time required for measurement even for different items to be analyzed.

It is preferred that the dispensing section include parts (tip, etc.) which contact a reagent and/or a sample capable of being exchanged. By replacing the parts with new ones at every measurement, the contamination of the cartridge to be used in a subsequent measurement can be easily prevented.

As aforementioned, it is preferred that the measurement be performed by attaching a bar code to the cartridge of the present invention and using an instrument provided with a mechanism for recognizing the bar code. By using an instrument which can recognize a barcode and automatically selecting an item for analyzing, automatic measurement of a plurality of items to be analyzed can be more easily and efficiently performed; for example, individually setting reaction temperature and photometric conditions become unnecessary, and the analysis of results of measurement can be easily performed.

EXAMPLE

Hereinafter, the present invention will be illustrated in more detail by way of examples. However, the following examples are merely for illustration and the scope of the present invention should not be construed as being limited by the following examples. It is obvious to one skilled in the art that any variations, improvements or modifications can be made to the present invention without departing from the spirit of the present invention.

Preparation Example 1

Preparation of Reagent and Solution

Respective reagents and solutions necessary for the measurement of HBs antigen (HBsAg), hepatitis C virus (HCV) antibody, human immunodeficiency virus (HIV) antibody, human T cell leukemia virus 1 (HTLV-1) antibody and *Treponema pallidum* (TP) antibody were prepared.

1. Preparation of Magnetic Particles

Anti-HBsAg polyclonal antibody was physically adsorbed on magnetic particles (0.3 µm) in 50 mM phosphate buffer (pH 4) and the resultant particles were treated in 0.2% BSA-containing Tris buffer (0.1 M pH 8) at 37° C. for 1 day to prepare anti-HBsAg antibody-bound magnetic particles.

Similarly, HCV antigen, HIV antigen, HTLV-1 antigen, and TP antigen were subjected to the same treatment as above to prepare HCV antigen-bound magnetic particles, HIV antigen-bound magnetic particles, HTLV-1 antigen-bound magnetic particles, and TP antigen-bound magnetic particles, respectively.

The prepared magnetic particles were suspended in 0.1 M Tris buffer (pH 8.0) and then used (concentrations were individually set for each item between 100 to 200 µg/ml).

2. Preparation of Labeled Antibody

Anti-HBsAg monoclonal antibody was bound to borvine alkaline phosphatase (ALP) by a maleimide method to prepare ALP-labeled HBsAg antibody. Similarly, anti-human IgG monoclonal antibody was used to prepare ALP-labeled anti-human IgG antibody. The prepared labeled antibodies were dissolved in 0.1 M Tris buffer (pH 8.0) and used (concentrations were individually set for each item between 0.2 to 0.5 µg/ml).

3. Preparation of Washing Solution 0.1 M Tris buffer (pH 8.0) containing 0.1% Tween 20 and 0.15 M NaCl was prepared.

4. Preparation of Diluting Solution 0.1 M Tris buffer (pH 8.0) containing 1% BSA and 0.15 M NaCl was prepared.

5. Luminescent Substrate

As a luminescent substrate, 25 mM AMPPD solution (Tropix Co.) was used.

Example 1

Measurements (A) of HBsAg, HCV Antibody, HIV Antibody, HTLV-1 Antibody and TP Antibody Measurements were performed by using a polystyrene-made cartridge shown in FIG. 1. After filling respective reagents and solutions prepared in 1 to 5 of Preparation Example 1 described above in a diluting well 1 (2), a diluting well 2 (3), a magnetic particles-containing well (4), a labeled antibody-containing well (6), a washing well 1 (5), a washing well 2 (7), and a photometric well (8), the top of each reagent-containing well was sealed with aluminum laminate foil. The position of filling and the filling amount were as follows.

TABLE 1

|  | Cartridge for HBsAg | Cartridge for HCV antibody | Cartridge for HIV antibody | Cartridge for HTLV-1 antibody | Cartridge for TP antibody |
|---|---|---|---|---|---|
| Sample-dispensing wells | Empty | Empty | Empty | Empty | Empty |
| Diluting well 1 | Empty | Sample-diluting solution 500 μl | Sample-diluting solution 500 μl | Sample-diluting solution 500 μl | Sample-diluting solution 500 μl |
| Diluting well 2 | Empty | Sample-diluting solution 335 μl | Sample-diluting solution 335 μl | Sample-diluting solution 335 μl | Sample-diluting solution 335 μl |
| Magnetic particles-containing well (Reaction well 1) | Anti-HBsAg antibody-bound magnetic particles 150 μl | HCV antigen-bound magnetic particles 150 μl | HIV antigen-bound magnetic particles 150 μl | HTLV-1 antigen-bound magnetic particles 150 μl | TP antigen-bound magnetic particles 150 μl |
| Washing well 1 | Washing solution 500 μl | Washing solution 500 μl | Washing solution 500 μl | Washing solution 500 μl | Washing solution 500 μl |
| Labeled antibody-containing well (Reaction well 2) | ALP-labeled anti-human HBsAg antibody 150 μl | ALP-labeled anti-human IgG antibody 150 μl | ALP-labeled anti-human IgG antibody 150 μl | ALP-labeled anti-human IgG antibody 150 μl | ALP-labeled anti-human IgG antibody 150 μl |
| Washing well 2 | Washing solution 500 μl | Washing solution 500 μl | Washing solution 500 μl | Washing solution 500 μ | Washing solution 500 μl |
| Photometric well | AMPPD solution 200 μl | AMPPD solution 200 μl | AMPPD solution 200 μl | AMPPD solution 200 μl | AMPPD solution 200 μl |

The prepared five types of reagent cartridges were concurrently measured by an automatic measuring instrument provided with quintuplet aspirating/dispensing mechanisms and quintuplet magnetic particles separating mechanisms in accordance with the following steps.

(1) Samples (negative control serum and positive control serum) were dispensed in an amount of 70 μl or more in respective sample-dispensing wells on the cartridge for HBsAg, cartridge for HCV antibody, cartridge for HIV antibody, cartridge for HTLV-1 antibody, and cartridge for TP antibody.

(2) The reagent cartridges having dispensed thereon a sample are set on an automatic measuring instrument. The arrangement of the reagent cartridges may be optional.

(3) The automatic measuring instrument was started.

(4) The automatic measuring instrument read a bar code attached to the reagent cartridge and recognized which analyzing item was selected. Thereafter, five reagent cartridges were concurrently subjected to the same process.

(5) The aluminum seal on the top of the reagent cartridge was pierced with a rod-like projection.

(6) 70 μl of sample was aspirated from a sample-dispensing well (1) and the whole amount of it was dispensed into the diluting well 1 (2). Further, by repeating aspiration and dispense operations in the diluting well 1 (2), a first stage diluting process was performed.

(7) 65 μl of the sample was aspirated from the diluting well 1 (2) and the whole amount of it was dispensed into the diluting well 2 (3). Further, by repeating aspiration and dispense operations in the diluting well 2 (3), a second stage diluting process was performed.

(8) 60 μl of sample was aspirated from the diluting well 2 (3), dispensed to a magnetic particles-containing well (4), and mixed with magnetic particles, followed by reaction at 42° C. for 10 minutes.

(9) In the magnetic particles-containing well (4), the magnetic particles were separated by using a magnet and moreover the magnetic particles were washed in a washing well 1 (5). Thereafter, the magnetic particles were separated therefrom by using a permanent magnet.

(10) The magnetic particles were dispensed into a labeled antibody-containing well (6), and were allowed to further react at 42° C. for 10 minutes.

(11) In the labeled antibody-containing well (6), the magnetic particles were separated by using a magnet and moreover the magnetic particles were washed in a washing well 2 (7). Thereafter, the magnetic particles were separated therefrom by using a permanent magnet.

(12) The magnetic particles were dispensed in a photometric well (8), mixed with AMPPD solution, and subjected to enzyme reaction at 42° C. for 5 minutes. Thereafter, the amount of luminescence was measured from above the photometric well by using a photo multiplier tube (PMT).

The aforementioned measurements were repeated for 12 days and reproducibility day after day was examined to obtain the following good results.

TABLE 2

|  |  | HBsAg | HCV antibody | HIV antibody | HTLV-1 antibody | TP antibody |
|---|---|---|---|---|---|---|
| Negative control serum | Average | 257 | 3,646 | 1,521 | 1,563 | 2,585 |
|  | Standard deviation | 17 | 425 | 199 | 199 | 291 |
|  | CV(%) | 6.5% | 11.7% | 13.1% | 12.7% | 11.3% |
| Positive control serum | Average | 45,035 | 43,601 | 72,983 | 215,806 | 34,571 |
|  | Standard deviation | 1,404 | 1,984 | 2,902 | 13,593 | 1,659 |
|  | CV(%) | 3.1%. | 4.6% | 4.0% | 6.3% | 4.8% |

(Numerical values indicate the intensity of luminescence.)

Example 2

Measurement (B) of HBsAg, HCV Antibody, HIV Antibody, HTLV-1 Antibody and TP Antibody Measurements were performed by using a polystyrene-made cartridge shown in FIG. 2. That is, sample-diluting solutions and reagents which participate in reaction (magnetic particles, labeled antibody, AMPPD) were filled in a different cartridge (hereinafter in some cases referred to as "reagents cartridge") than the cartridge of the present invention (hereinafter in some cases referred to as "reaction cartridge"). The measurements were performed such that the reagents were not physically bound and dilution of the samples was made in three stages. As reagents and solutions, those prepared in Preparation Example 1 described above were used.

(1) A reagent cartridge for HBsAg, a cartridge for HCV antibody, a reagent cartridge for HIV antibody, a reagent cartridge for HTLV-1 antibody, and a reagent cartridge for TP antibody were set in an automatic measuring instrument. The arrangement of the reagents cartridges may be optional. The reagent cartridges were filled with reagents and solutions, respectively, in advance as shown in Table 3 and sealed with aluminum laminate foil.

(2) The reaction cartridge was set in the instrument. Here, the reaction cartridge is an empty cartridge with neither diluting solution nor reagent being filled therein (without aluminum seal) so that it is common regardless of which item for analyzing is concerned.

(3) Samples (negative control serum and positive control serum) were dispensed in the sample-dispensing well (SD) of each reaction cartridge in correspondence with a line on each reagent cartridge in an amount of 115 µl or more.

(4) The automatic measuring instrument was started.

(5) The automatic measuring instrument read a bar code attached to the reagent cartridge and recognized which analyzing process was selected. Thereafter, five reagent cartridges and reaction cartridges corresponding to the reagent cartridges were concurrently subjected to the same process.

(6) The aluminum seal on the top of the reagent cartridge was pierced with a rod-like projection.

(7) Reagents were filled in the reaction cartridges from each reagent cartridge. The order of dispensing was determined in consideration of contamination of dispensing tips.

(8) First, 1,000 µl of washing solution was aspirated from a washing solution-containing well (WS) and 500 µl portions were dispensed into a washing well 1 (W1) and a washing well 2 (W2), respectively.

(9) 200 µl of AMPPD was aspirated from an AMPPD containing well (AMPPD) and the whole amount of it was dispensed into a photometric well (LM).

(10) 190 µl of a sample diluting solution was aspirated from the diluting solution containing well 1 (DS1) and the whole amount of it was dispensed into a diluting well 1 (D1). When the diluting solution containing well 1 (DS1) was empty, the diluting well 1 (D1) remained empty after this operation.

(11) 290 µl of a sample diluting solution was aspirated from the diluting solution containing well 1 (DS1) and the whole amount of it was dispensed into a sample diluting well 2 (D2). When the diluting solution containing well 1 (DS1) was empty, the diluting well 2 (D2) remained empty after this operation.

(12) 285 µl of a sample diluting solution was aspirated from the diluting solution-containing well 1 (DS1) and the whole amount of it was dispensed into a sample diluting well 3 (D3). When the diluting solution-containing well 1 (DS1) was empty, the diluting well 3 (D3) remained empty after this operation.

(13) 115 µl of the sample diluting solution was aspirated from the diluting solution-containing well 2 (DS2) and the whole amount of it was dispensed to the sample diluting well 1 (D1). When the diluting solution-containing well 2 (DS2) was empty, the amount of the diluting-solution in the diluting well 1 (D1) remained unchanged after this operation.

(14) 250 µl of a labeled antibody was aspirated from a labeled antibody-containing well (LA) and the whole amount of it was dispensed into a reaction well 2 (R2).

(15) 250 µl of magnetic particles suspension was aspirated from a magnetic particles-containing well (MP) and the whole amount of it was dispensed to a reaction well 1 (R1).

(16) By the above operations, all the necessary reagents were filled from the reagent cartridges to the reaction cartridges. Thereafter, sample dilution, reaction and photometric processes using the reaction cartridges proceeded.

(17) 115 µl of sample was aspirated from a sample-dispensing well (SD) and the whole amount of it was dispensed to the diluting well 1 (D1). Further, by repeating aspiration and dispense operations in the diluting well 1 (D1), a first stage diluting process was performed.

(18) 110 µl of the sample was aspirated from the diluting well 1 (D1) and the whole amount of it was dispensed into the diluting well 2 (D2). Further, by repeating aspiration and dispense operations in the diluting well 2 (D2), a second stage diluting process was performed.

(19) 105 µl of the sample was aspirated from the diluting well 2 (D2) and the whole amount of it was dispensed to the diluting well 3 (D3). Further, by repeating aspiration and dispense operations in the diluting well 3 (D3), a third stage diluting process was performed. By the above operations, finally a desired dilution as shown in Table 4 was obtained.

(20) 100 µl of the sample was aspirated from the diluting well 3 (D3) and the whole amount of it was dispensed into the reaction well 1 (R1), and mixed with magnetic particles, followed by reaction at 37° C. for 10 minutes.

(21) In the reaction well 1 (R1), the magnetic particles were separated by using a permanent magnet and moreover the magnetic particles were washed in a washing well 1 (W1). Thereafter, the magnetic particles were separated therefrom by using a permanent magnet.

(22) The magnetic particles were dispensed into a reaction well 2 (R2), mixed with a labeled antibody. In addition, after the mixing, they were allowed to react at 37° C. for 10 minutes.

(23) In the reaction well 2 (R2), the magnetic particles were separated by using a permanent magnet and moreover the magnetic particles were washed in a washing well 2 (W2). Thereafter, the magnetic particles were separated therefrom by using a permanent magnet.

(24) The magnetic particles were dispensed in a photometric well (LM), mixed with AMPPD solution, and subjected to enzyme reaction at 37° C. for 5 minutes. Thereafter, the amount of luminescence was measured from above the photometric well (LM) by using a photo multiplier tube (PMT).

TABLE 3

|  | HBsAg | HCV,HIV,HTLV-1 | TP |
|---|---|---|---|
| Diluting solution-containing well 1 | 0 μl | 800 μl | 0 μl |
| Diluting solution-containing well 2 | 0 μl | 150 μl | 150 μl |
| Washing solution-containing well | 1100 μl | 1100 μl | 1100 μl |
| Magnetic particles-containing well | 300 μl | 300 μl | 300 μl |
| Labeled antibody-containing well | 300 μl | 300 μl | 300 μl |
| AMPPD-containing well | 250 μl | 250 μl | 250 μl |

TABLE 4

|  | Filling amount of diluting solution | | | Sampling amount (introduction amount) |
|---|---|---|---|---|
|  | HBsAg | HCV,HIV, HTLV-1 | TP | |
| Diluting well 1 | 0 μl | 305 μl | 115 μl | 115 μl |
| Diluting well 2 | 0 μl | 290 μl | 0 μl | 110 μl |
| Diluting well 3 | 0 μl | 285 μl | 0 μl | 105 μl |
| Last dilution magnification | 1 time | 50 times | 2 times | 100 μl |

TABLE 5

|  |  | HBsAg | HCV antibody | HIV antibody | HTLV-1 antibody | TP antibody |
|---|---|---|---|---|---|---|
| Negative control serum | Triplicate measurement | 704 | 13,096 | 10,068 | 11,740 | 420 |
|  |  | 560 | 12,328 | 10,084 | 11,408 | 412 |
|  |  | 496 | 12,484 | 10,296 | 12,108 | 404 |
|  | Average | 587 | 12,636 | 10,149 | 11,752 | 412 |
|  | CV(%) | 18.2% | 3.2% | 1.3% | 3.0% | 1.9% |
| Positive control serum | Triplicate measurement | 272,316 | 372,308 | 870,088 | 2,668,518 | 82,272 |
|  |  | 260,004 | 363,888 | 919,080 | 2,719,068 | 83,844 |
|  |  | 266,800 | 364,948 | 930,576 | 2,567,712 | 89,089 |
|  | Average | 266,373 | 367,048 | 906,581 | 2,651,764 | 85,071 |
|  | CV(%) | 2.3% | 1.2% | 3.5% | 2.9% | 4.2% |

INDUSTRIAL APPLICABILITY

According to the present invention, measurements of a plurality of kinds of items to be analyzed with different dilutions in a sample can be performed concurrently by a uniform analyzing process. This leads to simplification of an automatic measuring instrument, reduction in cost, shortening of time required for measurement and enables easy measurement.

What is claimed is:

1. A measuring method for a component to be measured contained in a sample, comprising:
   providing a cartridge comprising at least two or more lines of well groups arranged in parallel or providing plural cartridges each having at least one line of well groups, wherein each well group comprises a diluting well for diluting a predetermined amount of the sample to a desired dilution, and a reaction well in which the component to be measured contained in the sample and a substance specifically reacting therewith are allowed to react, wherein a diluting solution is filled in the diluting well of each well group in a predetermined amount to provide the desired dilution depending on a type of the component to be measured and then sealing the cartridge or plural cartridges using a cartridge seal or cartridge seals;
   piercing the cartridge seal or cartridge seals and dispensing the predetermined amount of sample in the diluting well of each well group already filled with the predetermined amount of diluting solution with a dispensing mechanism comprising multiple dispensing elements in a uniform operation to thereby dilute the sample to the desired dilution in each diluting well of each well group;
   reacting the component to be measured in the diluted sample with the substance specifically reacting therewith; and
   measuring an amount of a reaction product.

2. A measuring method according to claim 1, wherein a plurality of kinds of different components to be measured are concurrently measured with regard to the two or more lines of well groups provided in the cartridge, or with regard to the at least one line of well groups provided by the plurality of cartridges.

3. A measuring method according to claim 1, wherein the plurality of cartridges are provided with at least one cartridge of the plurality of cartridges having at least one well filled with at least one of a reagent and a solution used in the measurement of the component to be measured contained in the sample.

4. A measuring method according to claim 1, wherein the reaction between the component to be measured and the substance specifically reacting therewith is an immunological reaction.

5. A measuring method according to claim 4, wherein the immunological reaction is a reaction in which the component to be measured in the sample and the substance immunologically specifically reacting therewith are allowed to react to form a first immune complex, and the first immune complex and a label immunologically specifically reacting therewith are allowed to react to form a second immune complex, and wherein the amount of the label in the second immune complex formed by the reaction is measured.

6. A measuring method according to claim 1, wherein the cartridge comprising the two or more lines of well groups arranged in parallel is provided.

7. A measuring method according to claim 1, wherein each well group further comprises at least one of a reagent-containing well for containing a reagent used in the measurement, a sample-dispensing well for dispensing the sample, a washing well for performing washing of a reaction product, and a measuring well for performing measurement of the reaction product.

8. A measuring method according to claim 1, wherein plural cartridges each having at least one line of well groups are provided.

* * * * *